United States Patent
Tsunori

(10) Patent No.: US 7,452,204 B2
(45) Date of Patent: Nov. 18, 2008

(54) REDUCED FRICTION BRACKET FOR ORTHODONTICS

(76) Inventor: Masahiro Tsunori, A706, 2-28-1 Honkomagome, Bunkyo-ku, Tokyo (JP)

( * ) Notice: Subject to any disclaimer, the term of this patent is extended or adjusted under 35 U.S.C. 154(b) by 0 days.

(21) Appl. No.: 11/177,581

(22) Filed: Jul. 8, 2005

(65) Prior Publication Data

US 2006/0257809 A1  Nov. 16, 2006

(30) Foreign Application Priority Data

May 11, 2005  (JP)  ............... 2005-138632

(51) Int. Cl.
*A61C 3/00* (2006.01)
(52) U.S. Cl. ............................ 433/9; 433/15
(58) Field of Classification Search ........... 433/8–10, 433/15–17, 11, 13
See application file for complete search history.

(56) References Cited

U.S. PATENT DOCUMENTS

| | | | | |
|---|---|---|---|---|
| 3,193,930 A * | 7/1965 | Bien | | 433/15 |
| 4,052,792 A * | 10/1977 | Biederman | | 433/8 |
| 4,565,526 A * | 1/1986 | Kawata et al. | | 433/8 |
| 5,062,794 A * | 11/1991 | Miura | | 433/10 |
| 5,160,261 A * | 11/1992 | Peterson | | 433/8 |
| 5,282,743 A * | 2/1994 | Miura | | 433/8 |
| 5,299,934 A * | 4/1994 | Suyama | | 433/8 |
| 5,380,196 A * | 1/1995 | Kelly et al. | | 433/8 |
| 5,456,599 A * | 10/1995 | Hanson | | 433/8 |
| 5,470,228 A * | 11/1995 | Franseen et al. | | 433/8 |
| 5,947,723 A * | 9/1999 | Mottate et al. | | 433/8 |
| 6,168,429 B1 * | 1/2001 | Brown | | 433/11 |
| 6,227,849 B1 * | 5/2001 | Brehm et al. | | 433/9 |
| 2002/0168601 A1 * | 11/2002 | Orikasa et al. | | 433/9 |
| 2002/0197581 A1 * | 12/2002 | Georgakis et al. | | 433/10 |
| 2003/0064342 A1 * | 4/2003 | Fukutomi | | 433/8 |
| 2006/0257809 A1 * | 11/2006 | Tsunori | | 433/10 |

* cited by examiner

*Primary Examiner*—Ralph A Lewis
(74) *Attorney, Agent, or Firm*—James E. Walton

(57) ABSTRACT

The bracket (11) comprises a body (21) having a ligaturing surface (21*a*) on which ligature by a wire is performed. A slot portion (22) for threading an arch wire (12) serving as a first wire extending over a plurality of teeth is provided on the ligaturing surface (21*a*) of the body (21). Wing portions (23) extending from the slot portion (22) in the direction generally perpendicular to a longitudinal direction of the slot portion (22) are provided. A ligature wire (26) serving as a second wire used in ligaturing the arch wire (12) is hitched round the wing portions (23). And guide portions (24) for guiding the ligature wire (26) to extend across the slot portion (22) are formed.

8 Claims, 2 Drawing Sheets

(a)    (b)

(a)    (b)    (c)

REDUCED FRICTION BRACKET FOR ORTHODONTICS

This application claims priority under 35 U.S.C. §119 to Japanese Patent Application No. JP 2005-138632, filed May 11, 2005. titled "Bracket for Orthodontics."

BACKGROUND OF THE INVENTION

1. Field of the Invention

The present invention relates to a bracket for orthodontics.

2. Description of Related Art

Conventionally, treatment of orthodontics has been performed in order to redress snaggleteeth causing troubles in occlusion and aesthetic terms and to reconstruct the occlusion. In the treatment, a bracket 1 shown in FIGS. 9 and 10 is fixed on surfaces of each tooth T, a metal arch wire 2 is threaded through a slot 1a which is a groove of the bracket 1, and a metal ligature wire 3 hitched round wings 1b (four of the wings 1b are illustrated here) of the bracket 1 squeezes the arch wire 2 (ligature). Thus, the tooth T on which the bracket 1 is fixed by the force of fastening the arch wire 2 is moved to the original position and redressed.

In the above-mentioned orthodontics, the tooth T is moved by sliding the arch wire 2 threaded through the slot 1a of the bracket 1 along the slot 1a, and therefore friction between the slot 1a and the arch wire 2 becomes a problem while ligaturing the teeth. Conventionally, development of manufacturing the slot 1a and the arch wire 2 using material with less frictional resistance has been worked on. However, the friction between the slot 1a and the arch wire 2 is hardly lessened under the current circumstances.

SUMMARY OF THE INVENTION

In the view of the above-mentioned facts, it is therefore an object of the present invention to provide a bracket for orthodontics capable of lessening the friction substantially while ligaturing the teeth.

A bracket for orthodontics of the present invention is characterized in comprising a body of a bracket having a ligaturing surface on which ligature by a wire is performed, a slot portion provided on the above-mentioned ligaturing surface of the above-mentioned body for threading a first wire extending over a plurality of teeth, a plurality of wing portions extending from the above-mentioned slot portion in the direction generally perpendicular to longitudinal direction of the above-mentioned slot portion for hitching a second wire used in ligaturing the first wire threaded though the above-mentioned slot portion, and a guide portion for guiding the above-mentioned second wire to extend across the above-mentioned slot portion.

According to the above-mentioned structure, the second wire can extend across the slot portion while ligaturing the teeth as the guide portion for guiding the second wire is provided in the body of the bracket. Thus, the second wire is prevented from squeezing the first wire. Consequently, the frictional resistance in ligaturing may be lessened substantially.

The bracket for orthodontics of the present invention preferably provides the above-mentioned guide portion extending from the above-mentioned wing portion. Additionally, the bracket for orthodontics of the present invention preferably provides the above-mentioned second wire guided by the above-mentioned guide portion apart from the above-mentioned first wire. Further, the bracket for orthodontics of the present invention can use metallic material for forming the above-mentioned guide portion.

With the present invention, a bracket capable of preventing the second wire from squeezing the first wire and achieving a substantial reduction of frictional resistance while ligaturing the teeth may be provided, in which the bracket comprises a body having a ligaturing surface on which ligature by a wire is performed, a slot portion provided on the above-mentioned ligaturing surface of the above-mentioned body of the bracket for threading a first wire extending over a plurality of teeth, a plurality of wing portions extending from the above-mentioned slot portion in the direction generally perpendicular to longitudinal direction of the above-mentioned slot portion for hitching a second wire used in ligaturing the first wire threaded though the above-mentioned slot portion, and a guide portion for guiding the above-mentioned second wire to extending over the upper portion of the above-mentioned slot portion.

The inventor of the present invention focused on the fact that the friction between the slot and the arch wire during the ligature is mainly caused by the structure of the slot in the bracket and found that the frictional resistance between the slot and the arch wire during the ligature may be substantially reduced by preventing the ligature wire from squeezing the arch wire during the ligature and thereby accomplished the present invention.

That is, the technical idea of the present invention is to provide a body of a bracket with guide portions for guiding a ligature wire which serves as a second wire and extends along upper portions of slot portions during ligaturing the teeth. Therefore, the second wire is prevented from squeezing an arch wire serving as a first wire and consequently frictional resistance during the ligature may be lessened substantially.

DETAILED DESCRIPTION OF THE PREFERRED EMBODIMENTS

Figure 1:
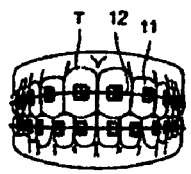
FIG. 1 is a front view for showing a state of performing a treatment of orthodontics using a bracket for orthodontics relating to an embodiment of the present invention.

Referring now to the drawings, preferred embodiments of the present invention are described more particularly. FIG. 1 is a front view for showing a state of performing a treatment of orthodontics using a bracket for orthodontics relating to an embodiment of the present invention. As it is shown in FIG. 1, a bracket 11 is fixed on a surface of each tooth T. For setting the bracket on the teeth, a method of fixing the bracket 11 on a tooth T by coating a reverse surface (a backside of a ligatured surface) of the bracket 11 with an adhesive and attaching the surface to the surface of the tooth T and the like are acceptable. An arch wire 12 which serves as a first wire extends over the teeth through each bracket 11. The arch wire 12 is secured by clasps 13 covering surfaces of molars on both ends.

Figure 2:
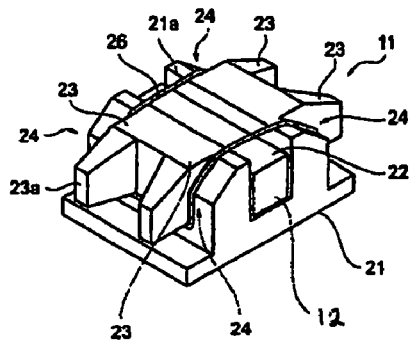
FIG. 2 is a perspective view for showing the bracket relating to an embodiment of the present invention.

FIG. 2 is a perspective view for showing the bracket relating to an embodiment of the present invention. The bracket 11 shown in FIG. 2 comprises a body 21 having a ligature surface 21a on which ligature by a wire is performed. A fixing surface adhered on the tooth T is provided on the reverse side of the ligature surface 21a as mentioned above. A slot portion 22 for threading the arch wire 12 serving as a first wire extending over a plurality of teeth is provided in the ligaturing surface 21a of the body 21 of the bracket 11. In the structure shown in FIG. 2, the slot portion 22 consists of a groove formed along the arch wire 12 in the axial direction. And a wing portion 23 extending from the slot portion 22 in the direction generally perpendicular to longitudinal direction of the slot portion 22 is provided on the ligature surface 21a. A plurality (four) of wing portions 23 are provided. That is, two wing portions are provided on each longitudinal side of the slot portion 22. A ligature wire 26 provided as a second wire used in ligaturing the arch wire 12 may be hitched round the wing portions 23. Additionally, guide portions 24 for guiding the ligature wire 26 across the slot portion 22 are formed. The guide portions 24 comprises of notches provided beside the wing portions 23, in the present embodiment. Therefore, in the event of ligaturing the arch wire 12, the ligature wire 26 is hitched (along the side closer to the tooth) round each of two adjacent wing portions 23 protruding from the body 21 and is guided across the slot portion 22 by the guide portions 24.

Figure 3:
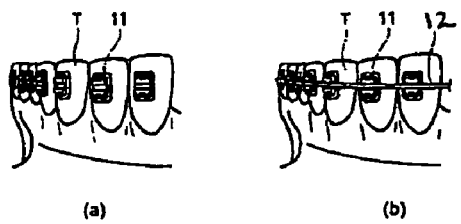
FIGS. 3(a) and 3(b) are drawings for explaining a manner of performing ligature by using the bracket relating to an embodiment of the present invention.
Figure 4:
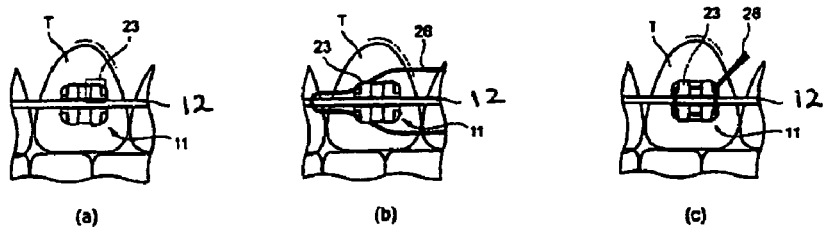
FIGS. 4(a) through 4(c) are drawings for explaining a manner of performing the ligature by using the bracket relating to an embodiment of the present invention.

The bracket 11 for orthodontics having the structure as mentioned above is fixed on the surfaces of each tooth T as shown in FIG. 3(a). And arch wire 12 is threaded through the slot portion 22 of each bracket 11 and secured. Thereafter, the ligature wire 26 is hitched round the bracket via the wing portions 23 shown in FIG. 4(a) provided in four corners of the bracket 11 as shown in FIG. 3(b). In the above-mentioned event, the ligature wire 26 is wound around the area of body 21 which is closer to the tooth T than the wing portions 23a (see FIGS. 2, 4a, 4c) extending like eaves from the wing portions 23 and is secured to the wing bracket 11. Incidentally, the above-mentioned method of securing the ligature wire 26 to the bracket 11 is an example and other methods are also acceptable.

Figure 5:
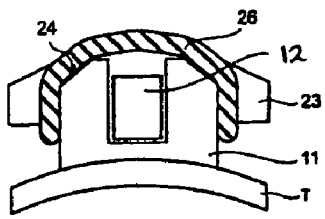
FIG. 5 is a drawing for showing a state after performing the ligature by using the bracket relating to an embodiment of the present invention.
Figure 9:
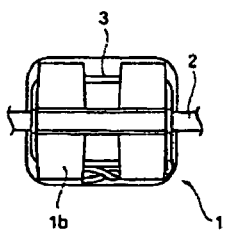
FIG. 9 is a front view for showing a state of performing orthodontics using a conventional bracket.
Figure 10:
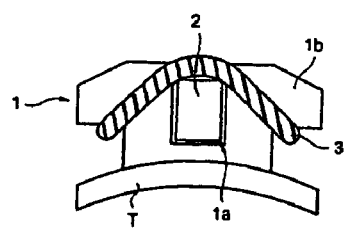
FIG. 10 is a side view for showing a state of performing orthodontics using a conventional bracket.

A state illustrated in FIG. 5 is brought about in consequence of performing the ligature using the bracket for orthodontics relating to the present invention. That is, the ligature wire 26 extends across the slot portion 22 along the guide portions 24 of the wing portions 23 at a point where the ligature wire 26 intersects the arch wire 12. Therefore, the ligature wire 26 and the arch wire 12 cross each other apart, which is different from the state shown in FIG. 9. Consequently, the arch wire 12 is unaffected by the ligature using the ligature wire 26, that is, the arch wire 12 is not affected by the force exerted by the ligature wire 26 during the ligature. Accordingly, the arch wire 12 is not squeezed with the ligature wire 26, thereby reducing the frictional resistance during the ligature.

Figure 6:
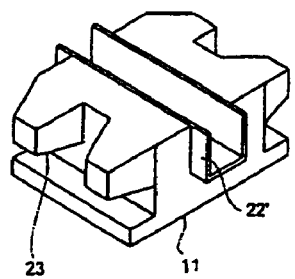
FIG. 6 is a perspective view for showing another example of the bracket relating to an embodiment of the present invention.
Figure 7:
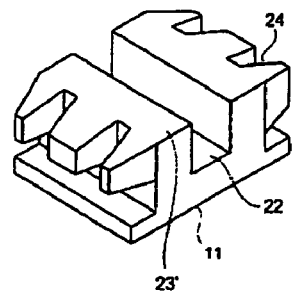
FIG. 7 is a perspective view for showing still another example of the bracket relating to an embodiment of the present invention.

The bracket for orthodontics of the present invention can be practiced not only with the structure shown in FIG. 2 but also with various modifications. For example, the bracket 11 having a slot portion 22' for threading the arch wire 12 through as shown in FIG. 6 is also acceptable, in which the slot portion 22' juts out from the bracket along longitudinal direction of the arch wire 12. In the above-mentioned event, an extended part of the slot portion 22' protruding from the body of the bracket 11 also serves as a guide portion. That is, the ligature wire 26 is hitched around the bracket 11 along the extended part of the slot portions 22'. And the structure shown in FIG. 2 with the guide portions provided beside each of the wing portions 23 can be modified for a structure providing fewer wing portions 23' (two of them in FIG. 7) with a plurality of guide portions 24 (two of them) at each wing portions 23' as shown in FIG. 7. Further, base portions for guiding the ligature wire 26 apart from the arch wire 12 can be provided at laterals of the wing portions 23. With the structures mentioned above, the ligature wire 26 and arch wire 12 are provided without making contact. Therefore, the ligature wire 26 is prevented from squeezing the arch wire 12, thereby reducing the frictional resistance during the ligature substantially.

Figure 8:
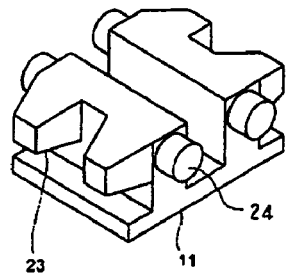
FIG. 8 is a perspective view for showing an example of a bracket of the present invention having guide portions manufactured of metallic material.

Further, the bracket for orthodontics of the present invention can be practiced with another modification as shown in FIG. 8. That is, the guide portions 24 formed of metal rod-like bodies manufactured of material such as stainless steel and the like can be inserted into the body of the bracket 11. And both ends of each rod-like body protruding through the surface of the body of the bracket 11 are provided for guiding the ligature wire 26 manufactured of metallic material. In the above-mentioned structure, the guide portions 24 provide high strength against the force applied by the ligature wire wound round the guide portions 24. Therefore, an endurance of the bracket for orthodontics of the present invention can be enhanced.

The structures and materials named in the above-mentioned embodiment are indicated as examples. Additionally, the present invention is not confined within the above-mentioned embodiments and can be practiced with modification within the spirit and scope of the appended claims.

What is claimed is:

1. A bracket for orthodontics, comprising:
   a base portion having a front side and a substantially planar back surface opposite the front side;
   an upper body portion extending to a distal end thereof from the front side of the base portion;
   a lower body portion extending to a distal end thereof from the front side of the base portion, the lower body portion being separated from the upper body portion so as to form a first longitudinal slot configured to receive an arch wire, the first longitudinal slot having a base defined by a first front surface of the front side of the base portion;
   an upper wing portion extending up from the distal end of the upper body portion, the upper wing portion being separated from a second front surface of the front side of the base portion so as to form a second longitudinal slot;
   a lower wing portion extending down from the distal end of the lower body portion, the lower wing portion being seperated from a third front surface of the front side of the base portion so as to form a third longitudinal slot; and a first cylindrical guide post extending out from each side of the distal end of the upper body portion and a second cylindrical guide post extending out from each side of the distal end of the lower body portion, the first and second cylindrical guide posts being substantially parallel to the first longitudinal slot.

2. The bracket for orthodontics according to claim 1, wherein the guide posts are formed of a metal material.

3. The bracket for orthodontics according to claim 2, wherein the metal material is stainless steel.

4. The bracket for orthodontics according to claim 1, wherein the first cylindrical guide post extending out from each side of the upper body portion is formed by a first rod passing through the upper body portion, and the second cylindrical guide post extending out from each side of the lower body portion is formed by a second rod passing through the lower body portion.

5. The bracket for orthodontics according to claim 1, further comprising:

a channel portion extending out from each side of the base portion so as to longitudinally extend the first longitudinal slot.

6. The bracket for orthodontics according to claim 1, wherein the upper wing portion is formed by a plurality of upwardly extending tabs and the lower wing portion is formed by a plurality of downwardly extending tabs.

7. The bracket for orthodontics according to claim 1, wherein the first cylindrical guide post extends out from each side of the upper body portion substantially adjacent to the first longitudinal slot and the second cylindrical guide post extends out from each side of the lower body portion substantially adjacent to the first longitudinal slot.

8. The bracket for orthodontics according to claim 1, wherein the upper body portion includes an intermediate portion thereof that extends between the front side of the base portion and the first cylindrical guide post, and the lower body portion includes an intermediate portion thereof that extends between the front side of the base portion and the second cylindrical guide post.

* * * * *